(12) United States Patent
Peterson et al.

(10) Patent No.: US 9,615,995 B2
(45) Date of Patent: Apr. 11, 2017

(54) CPR FEEDBACK METHOD AND APPARATUS

(71) Applicant: Cardiac Science Corporation, Waukesha, WI (US)

(72) Inventors: Peter Peterson, Silverado, CA (US); Kenneth F. Olson, Knoxville, TN (US)

(73) Assignee: Cardiac Science Corporation, Waukesha, WI (US)

( * ) Notice: Subject to any disclaimer, the term of this patent is extended or adjusted under 35 U.S.C. 154(b) by 503 days.

(21) Appl. No.: 14/094,124

(22) Filed: Dec. 2, 2013

(65) Prior Publication Data
US 2014/0163436 A1   Jun. 12, 2014

Related U.S. Application Data

(60) Continuation of application No. 13/209,701, filed on Aug. 15, 2011, now Pat. No. 8,600,522, which is a
(Continued)

(51) Int. Cl.
*A61H 31/00* (2006.01)
*A61N 1/39* (2006.01)

(52) U.S. Cl.
CPC ......... *A61H 31/005* (2013.01); *A61H 31/007* (2013.01); *A61N 1/39* (2013.01);
(Continued)

(58) Field of Classification Search
CPC .... A61H 31/00; A61H 31/004; A61H 31/007; A61H 31/005; A61H 2201/5007;
(Continued)

(56) References Cited

U.S. PATENT DOCUMENTS 3,859,984 A * 1/1975 Langley ............ A61B 8/02
                                                 310/334
4,059,099 A   11/1977 Davis
(Continued)

FOREIGN PATENT DOCUMENTS

EP          1491176 A1     12/2004
JP          10-507108 A     7/1998
(Continued)

OTHER PUBLICATIONS

AED—Specialized Defibrillator Products, Zoll® Advancing Resuscitation Today™, Webpage printout dated Mar. 27, 2007, www.zoll.com, 3 Pgs.
(Continued)

*Primary Examiner* — Justine Yu
*Assistant Examiner* — Timothy Stanis
(74) *Attorney, Agent, or Firm* — Patterson Thuente Pedersen, P.A.

(57) ABSTRACT

The present invention comprises a cardiopulmonary resuscitation (CPR) feedback device and a method for performing CPR. A chest compression detector device is provided that measures chest compression during the administration of CPR. The chest compression detector device comprises a signal transmitter operably positioned on the chest of the patient and adapted to broadcast a signal, and a signal receiver adapted to receive the signal. The chest compression detector device also comprises a processor, operably connected to the signal transmitter and the signal receiver. The processor repeatedly analyzes the signal received to determine from the signal a series of measurements of compression of the chest, and feedback is provided to the rescuer based on the series of measurements.

5 Claims, 11 Drawing Sheets

Related U.S. Application Data division of application No. 11/420,515, filed on May 26, 2006, now Pat. No. 8,010,190.

(52) U.S. Cl.
CPC .... *A61H 2031/002* (2013.01); *A61H 2201/10* (2013.01); *A61H 2201/5007* (2013.01); *A61H 2201/5043* (2013.01); *A61H 2201/5048* (2013.01); *A61H 2201/5058* (2013.01); *A61H 2201/5097* (2013.01); *A61H 2230/00* (2013.01); *A61H 2230/207* (2013.01)

(58) Field of Classification Search
CPC ........ A61H 2201/5058; A61H 2230/00; A61N 1/39
See application file for complete search history.

(56) References Cited

U.S. PATENT DOCUMENTS

| | | | |
|---|---|---|---|
| 4,095,590 A | | 6/1978 | Harrigan |
| 4,554,910 A | | 11/1985 | Lally |
| D290,396 S | | 6/1987 | Jones et al. |
| 4,967,751 A | * | 11/1990 | Sterzer ................. A61B 5/0507 600/407 |
| 5,131,399 A | * | 7/1992 | Sciarra ................. A61B 5/1135 128/903 |
| 5,295,481 A | | 3/1994 | Geeham |
| 5,405,361 A | | 4/1995 | Persson |
| 5,496,257 A | | 3/1996 | Kelly |
| 5,588,439 A | | 12/1996 | Hollub |
| 5,589,639 A | | 12/1996 | D'Antonio et al. |
| 5,645,522 A | | 7/1997 | Lurie et al. |
| 6,125,299 A | | 9/2000 | Groenke et al. |
| 6,306,107 B1 | | 10/2001 | Myklebust et al. |
| 6,351,671 B1 | | 2/2002 | Myklebust et al. |
| 6,390,996 B1 | | 5/2002 | Halperin et al. |
| 6,397,104 B1 | | 5/2002 | Miller et al. |
| D458,376 S | | 6/2002 | Rouns et al. |
| 6,427,685 B1 | | 8/2002 | Ray, II |
| 6,599,258 B1 | | 7/2003 | Bystrom et al. |
| 6,662,056 B2 | | 12/2003 | Picardo et al. |
| D485,360 S | | 1/2004 | Faller et al. |
| D490,156 S | | 5/2004 | Fischer et al. |
| D490,526 S | | 5/2004 | Jonsen |
| D492,782 S | | 7/2004 | Faller et al. |
| 6,807,442 B1 | | 10/2004 | Myklebust et al. |
| D498,848 S | | 11/2004 | Vaisnys et al. |
| 6,827,695 B2 | | 12/2004 | Palazzolo et al. |
| 6,858,016 B2 | | 2/2005 | Davaris et al. |
| 6,874,621 B2 | | 4/2005 | Solosko et al. |
| D511,384 S | | 11/2005 | Masuda |
| 7,016,727 B2 | | 3/2006 | Powers et al. |
| 7,041,062 B2 | | 5/2006 | Friedrichs et al. |
| 7,108,665 B2 | | 9/2006 | Halperin et al. |
| 7,220,235 B2 | | 5/2007 | Geheb et al. |
| 7,245,974 B2 | | 7/2007 | Dupelle et al. |
| RE40,471 E | | 8/2008 | Groenke et al. |
| 7,489,972 B2 | | 2/2009 | Denney et al. |
| 7,650,181 B2 | | 1/2010 | Freeman et al. |
| 8,010,190 B2 | | 8/2011 | Peterson et al. |
| 8,600,522 B2 | | 12/2013 | Peterson et al. |
| 2003/0023274 A1 | | 1/2003 | Chesley et al. |
| 2003/0036044 A1 | | 2/2003 | Pastrick et al. |
| 2003/0114885 A1 | | 6/2003 | Nova et al. |
| 2003/0167075 A1 | | 9/2003 | Fincke |
| 2004/0049235 A1 | | 3/2004 | Deno et al. |
| 2004/0066302 A1 | | 4/2004 | Menard et al. |
| 2004/0167389 A1 | * | 8/2004 | Brabrand ................. A61B 8/08 600/407 |
| 2004/0210171 A1 | | 10/2004 | Palazzolo et al. |
| 2004/0267325 A1 | * | 12/2004 | Geheb ..................... A61B 5/11 607/5 |
| 2005/0043763 A1 | | 2/2005 | Marcovecchio et al. |
| 2006/0009717 A1 | | 1/2006 | Hall et al. |
| 2006/0009809 A1 | | 1/2006 | Marcovecchio et al. |
| 2006/0025823 A1 | | 2/2006 | Jonsen |
| 2006/0058846 A1 | | 3/2006 | Smirles et al. |
| 2006/0272095 A1 | | 12/2006 | Kornaker |
| 2007/0088233 A1 | | 4/2007 | Wood |
| 2007/0112389 A1 | | 5/2007 | Jonsen |
| 2008/0071316 A1 | | 3/2008 | Freeman |
| 2008/0097546 A1 | | 4/2008 | Powers et al. |
| 2008/0300518 A1 | | 12/2008 | Bowes |
| 2009/0125074 A1 | | 5/2009 | Ochs et al. |
| 2009/0254136 A1 | | 10/2009 | Powers |

FOREIGN PATENT DOCUMENTS

| | | |
|---|---|---|
| JP | 2005-532122 A | 10/2005 |
| KR | 20000064418 A | 11/2000 |
| KR | 20010032189 A | 4/2001 |
| WO | WO 00/27464 | 5/2000 |
| WO | WO 01/08629 A1 | 2/2001 |
| WO | WO 02/22017 A1 | 3/2002 |
| WO | WO 2008/015624 A2 | 2/2008 |
| WO | WO 2008/025995 A2 | 3/2008 |
| WO | WO 2009/089096 A2 | 7/2009 |

OTHER PUBLICATIONS

Webpage printout entitled: "'It's a matter of life . . . ' Features and Benefits Cpr Ezy", Webpage printout dated Jun. 1, 2006, www.cprezy.com, 6 Pgs.

EP Office Action Cited in European Application No. 07290669.6-2318, dated Sep. 7, 2012, 4 Pgs.

EP Office Action Cited in European Application No. 07290669.6-2318, dated Oct. 26, 2010, 5 Pgs.

EP Office Action Cited in European Application No. 07290669.6-2318, dated Sep. 20, 2007, 9 Pgs.

* cited by examiner

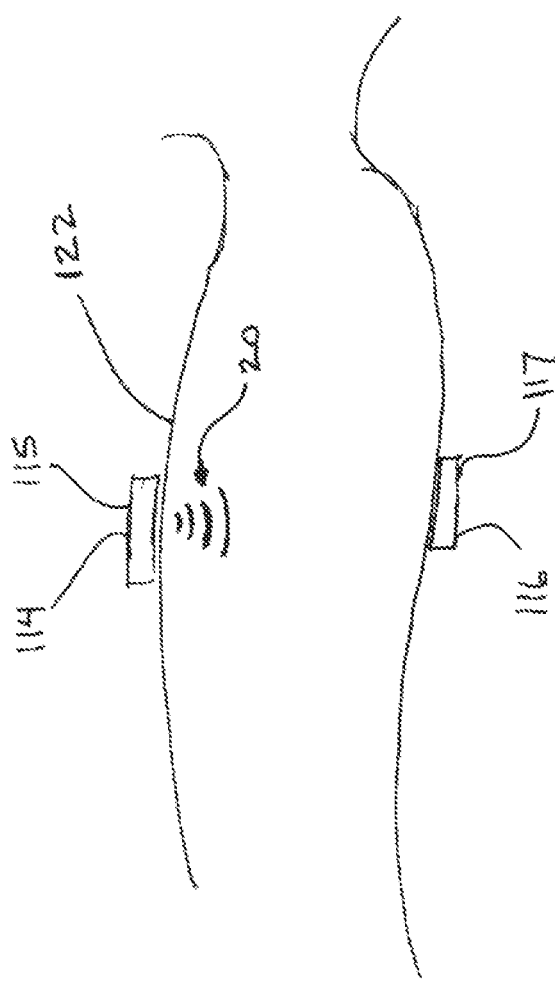

CPR FEEDBACK METHOD AND APPARATUS

RELATED APPLICATION

This application is a continuation of U.S. patent application Ser. No. 13/209,701, filed Aug. 15, 2011, now U.S. Pat. No. 8,600,522, issued Dec. 3, 2013, which is a divisional of U.S. patent application Ser. No. 11/420,515 filed May 26, 2006, now U.S. Pat. No. 8,010,190, issued Aug. 30, 2011, which are hereby fully incorporated herein by reference.

FIELD OF THE INVENTION

The present invention relates to devices and techniques useful for assisting in the administration of cardiopulmonary resuscitation (CPR). More particularly, the present invention relates to a device and method for using ultrasonic signals to determine the depth of chest compression during CPR.

BACKGROUND OF THE INVENTION

CPR is a technique used by a rescuer in an emergency situation to get oxygen into a victims blood when that persons heart has stopped beating and/or they are not breathing spontaneously. When performing CPR the rescuer creates blood circulation in the victims body by periodically compressing the victims chest.

The American Heart Association (AHA) recommends that the rescuer press down on the sternum with a force sufficient to depress it between 1.5 and 2.0 inches. The current recommended rate for these periodic depressions is 100 times a minute, and 30 chest compressions should be given for every two rescue breaths. Chest compressions produce blood circulation as the result of a generalized increase in intrathoracic pressure and/or direct compression of the heart. The guidelines state "blood circulated to the lungs by chest compressions will likely receive enough oxygen to maintain life when the compressions are accompanied by properly performed rescue breathing." A victim can be kept alive using CPR provided the rescuer(s) are able to continue delivering properly performed chest compressions and rescue breaths.

Administering CPR is a challenging and physically demanding procedure which is performed under stressful life and death circumstances. Performing chest compressions and rescue breaths is a also a physically demanding task, and can be difficult to properly coordinate. The quality of chest compressions and rescue breaths delivered to a patient can degrade for a number of reasons, including fatigue, lack of visual references, and rescue situation stresses. As rescuers become fatigued, they may not realize that they are compressing a patient's chest with inadequate force. The more fatigued a rescuer becomes, the less he may be compressing a patient's chest, and the more likely the effectiveness of the CPR is reduced.

To be most effective, the rescuer must attempt to keep the chest compressions uniform both in terms of the time between successive chest compressions and the amount of force used for each compression. Keeping uniform intervals for chest compressions is difficult the longer the CPR must be administered as the stresses associated with a rescue situation can cause the rescuer's sense of time to be distorted. Keeping the chest compressions uniform in terms of force is difficult not only because of fatigue, but also because it is difficult for the rescuer to estimate the force being applied based on the distance which the chest is being compressed. Much of the difficulty in estimating the distance which the chest is being compressed stems from the relative position of the rescuer and the victim. When performing chest compressions, the rescuer positions his or her shoulders directly above the victim's chest, and pushes straight down on the sternum. In this position, the rescuer's line of sight is straight down at the victim's chest. With this line of sight, the rescuer has no visual reference point to use as a basis for estimating the distance that he or she is compressing the chest.

The aforementioned problems may be compounded by a number of factors, such as when the length of time that CPR is being administered increases, and when the rescuer is not accustomed to rescue situations (for example when CPR is being performed by a lay person or a relatively inexperienced rescuer).

A number of devices have been proposed to assist a rescuer in applying CPR, as described, for example, in U.S. Pat. No. 6,125,299 to Groenke et al. Most of these devices measure either the force applied to a patient's chest, or measure the acceleration of the patient's chest (or rescuer's hand), or both. The measured force may be compared to a known desired value, and a prompt may be issued from the device instructing a rescuer to compress the patient's chest harder or softer. Displacement of a patient's chest can be calculated by double integrating a measured acceleration, and a prompt may be issued from the device instructing a rescuer to compress the patient's chest harder or softer. Many prior art devices also measure the frequency of chest compressions given, and are able to prompt a rescuer to increase or decrease the rate of compressions being administered.

Although measuring acceleration is an acceptable method of determining chest compression during CPR, the method is not without its flaws. For example, signal error, external acceleration error, and drift error in the compression starting points can all create inaccuracies in chest compression measurement. External acceleration error can arise from use of the accelerometer in a moving vehicle such as an ambulance, or from unusual patient attitudes, such as partially sitting up.

For these reasons, there is a need in the art for a practical device that more accurately measures the compression of a patient's chest during CPR, and provides feedback to a rescuer in the event that the displacement and frequency of chest compressions falls outside a preset criteria. A device of this type will provide rescuers with coaching which will enable them to deliver chest compressions consistently and beneficently.

SUMMARY OF THE INVENTION

The present invention, through various embodiments, provides a cardiopulmonary resuscitation (CPR) feedback device and a method for performing CPR. In one embodiment, a chest compression detector device is provided that measures chest compression during administration of CPR. The chest compression detector device comprises a signal transmitter operably positioned on the chest of the patient and adapted to broadcast a signal, and a signal receiver adapted to receive the signal. The chest compression detector device also comprises a processor, operably connected to the signal transmitter and the signal receiver. The processor repeatedly analyzes the signal received to determine from the signal a series of measurements of compression of the chest, and feedback is provided to the rescuer based on the series of measurements.

The CPR feedback device according to another embodiment is used in conjunction with an automatic external defibrillator (AED). The device includes a chest compression sensor on the chest of a patient, adapted to broadcast a signal toward the spine of a patient and adapted to receive a reflection of the signal. The chest compression sensor is in electrical communication with a control system of the AED, the control system processing a signal communicated from the chest compression sensor related to the magnitude of the chest compressions and to the frequency of chest compressions. The AED also includes a prompting means operably coupled to the AED control system for receiving communication signals from the AED control system and for communicating prompts to the rescuer for use by the rescuer in resuscitating the victim. The prompts are related to the signal communicated to the AED control system by the chest compression sensor.

The present invention also comprises a method of performing cardiopulmonary resuscitation on a patient. The method includes the steps of providing a compression detection device proximate the sternum of the patient such that the device moves in unison with the chest of the patient during compression of the chest, broadcasting a signal from the compression detection device, receiving the signal at the compression detection device, compressing the chest of a patient, using a processor operably in communication with the compression detection device to determine from the signal a series of measurements of compression of the chest relative to the spine of the patient as the step of compressing the chest of the patient is performed, and automatically providing feedback to a rescuer performing the step of compressing the chest of the patient as part of cardiopulmonary resuscitation in response to the series of measurements that advises the rescuer whether the step of compressing the chest is being performed within a predetermined set of guidelines.

BRIEF DESCRIPTION OF THE DRAWINGS

FIG. 11 is a side view of the measuring device applied to a patient according to an embodiment of the invention.

DETAILED DESCRIPTION OF THE INVENTION

Figure 1:
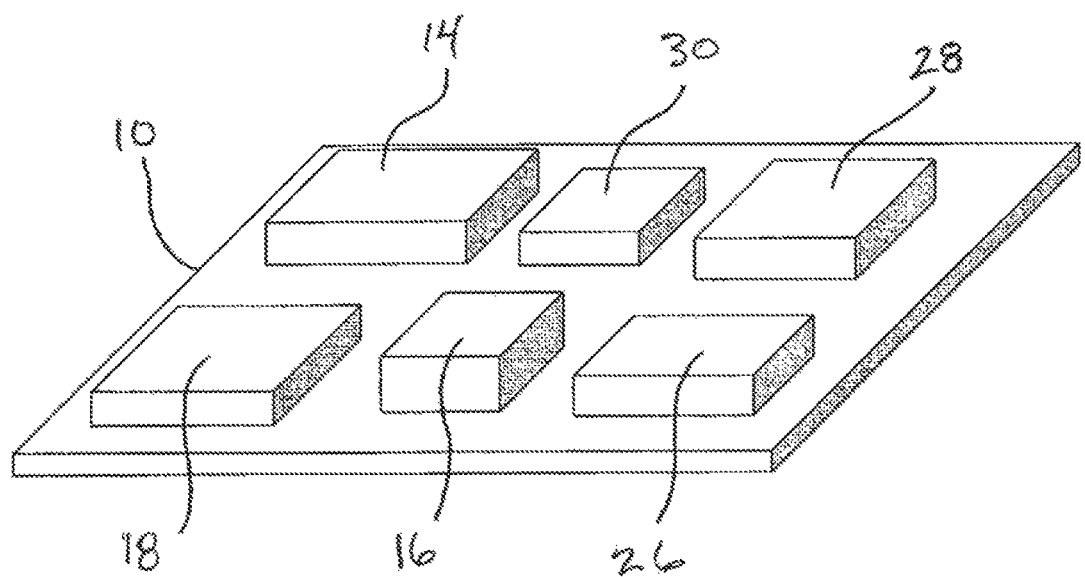
FIG. 1 is a perspective view of a chest compression detection device according to one embodiment of the present invention.

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

Referring to FIGS. 1-5, a chest compression detection device 10 is depicted. Device 10 includes a signal transmitter 14, a signal receiver 16, and a processor 18. In one embodiment, device 10 comprises an ultrasonic transducer. Transmitter 14 and receiver 16 are integrated into device 10. Processor 18 is operably coupled to both transmitter 14 and receiver 16. Processor 18 instructs transmitter 14 to send out an ultrasonic pulse 20, then counts the elapsed time for pulse 20 to reach receiver 16. Processor 18 can then calculate the distance of an object from device 10. Device 10 further includes an audio speaker 26, a power source 28, and may include a communicator 30. Power source 28 provides electrical power to all components in device 10.

Device 10 is placed on a victim's chest 22, in the location where chest compressions are to be administered. In one embodiment, device 10 is preferably located on the victim's sternum, generally between the victim's nipples, and in line with a victim's spine 24. A rescuer places his hands over device 10 and begins to administer chest compressions. Processor 18 instructs transmitter 14 to emit ultrasonic pulses 20. Pulses 20 are directed towards victim's spine 24, reflected, and received by receiver 16. Processor 18 counts the time it takes for pulse 20 to travel from transmitter 14 to receiver 16. Knowing the velocity at which sound waves travel, processor 18 can then calculate the distance that pulse 20 traveled. By collecting data of the distance traveled by many successive pulses, processor 18 can determine the amount that a chest 22 is being compressed by a rescuer. In one embodiment, the number of pulses 20 emitted per second is sufficient to give processor 18 sufficient data to accurately calculate chest compression depth. Once processor 18 has calculated chest compression depth, processor 18 compares that depth to a desired range of compression depth.

In order for CPR to be effective, chest compressions are preferably between one and one half (1.5) inches and two (2) inches. In the event that processor 18 determines chest 22 is not being compressed enough, processor 18 is adapted to provide feedback to the rescuer preferably through speaker 26. Similarly, if processor 18 determines that chest 22 is being over-compressed, processor 18 uses speaker 26 to provide feedback to the rescuer. Such feedback may be in the form of a voice prompt stating "push harder" in the event of under-compression of chest 22, or "push softer" in the event of over-compression of chest 22. Such feedback may also be some other audible prompt, such as beeps, or may include visual instructions, tactile feedback, or any combination thereof.

Processor 18 is also adapted to monitor the rate at which compressions are given and provide feedback to a rescuer if the rate of chest compressions falls outside of a predetermined range of rates. If the rate of chest compressions being delivered by the rescuer is less than the desired range, processor 18 causes speaker 26 to provide feedback to the rescuer, such as with a voice prompt stating "push faster," or other feedback prompt. If the rate of chest compressions being delivered by the rescuer is greater than the desired range, processor 18 causes speaker 26 to provide feedback to the rescuer, such as with a voice prompt stating "push slower," or other feedback prompt. It should be apparent that audio speaker 26 may be supplemented with, or replaced by, various indicators such as lights, a visual display, vibrating mechanism, and so on.

Figure 2:
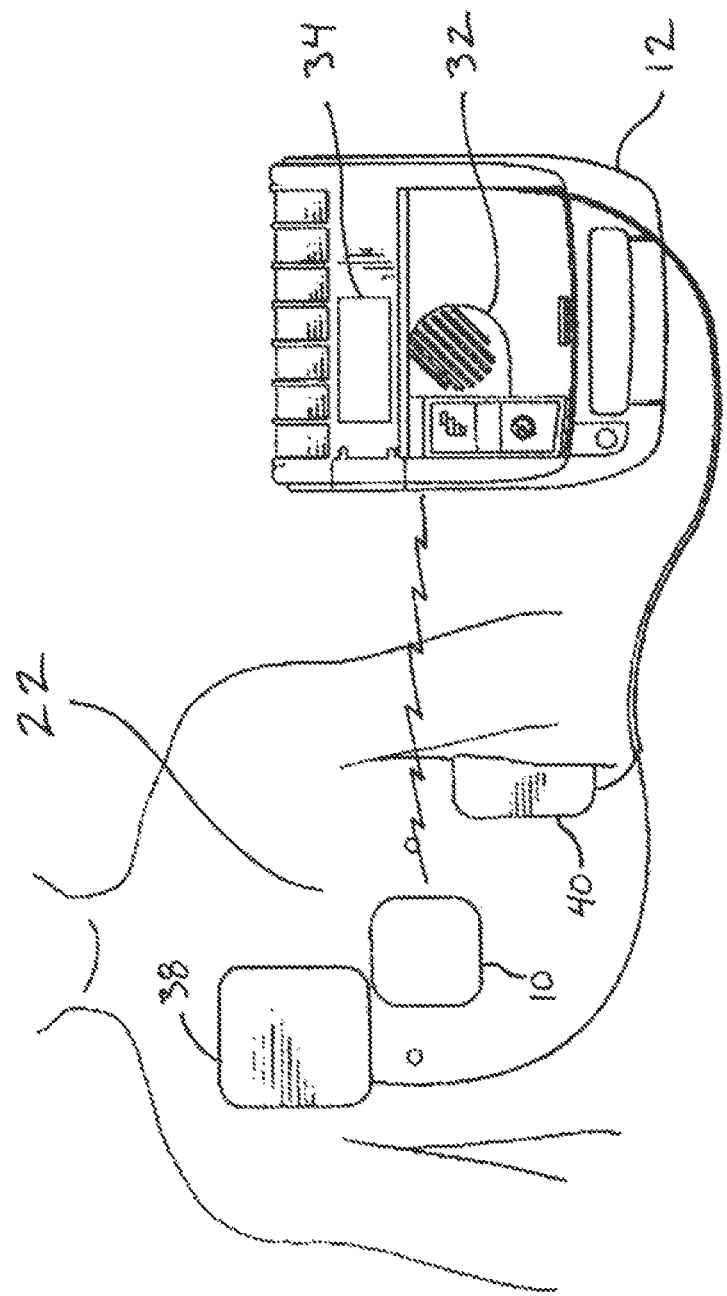
FIG. 2 is a perspective view of a measurement device applied to a patient being used with an automatic external defibrillator according to one embodiment of the present invention.
Figure 3:
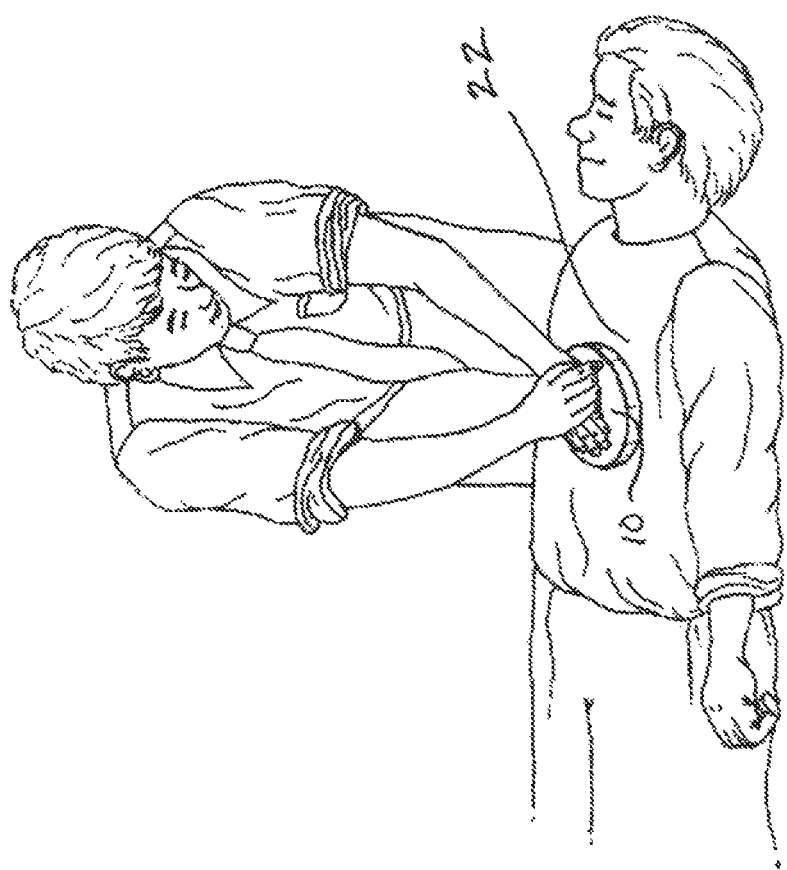
FIG. 3 is a perspective view of a measurement device being used on a patient.

In another embodiment of the present invention depicted in FIG. 2, device 10 does not include a speaker, rather device 10 includes a communicator 30. Communicator 30 is adapted to communicate chest compression data to automatic external defibrillator (AED) 12, using wireless means such as acoustic signals, optical signals, Bluetooth, IR, or RF. AED 12 includes an audio speaker 32 and/or a visual display 34. Audio speaker 32 and visual display 34 are each adapted to provide feedback to a rescuer in response to the chest compression data received from communicator 30 of device 10.

Figure 5:
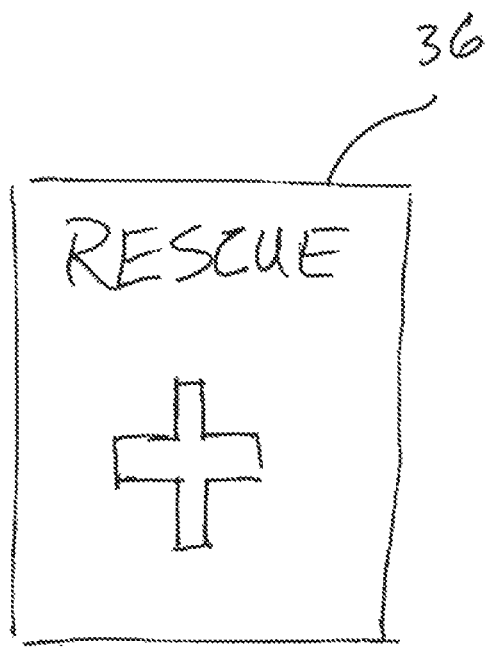
FIG. 5 is a perspective view of a rescue kit according to one embodiment of the present invention.

In such an embodiment, device 10 may comprise part of a rescue kit 36, depicted in FIG. 5. Rescue kit 36 may include basic first aid items such as a face shield, rubber gloves, scissors, and so on, in addition to a chest compression detection device. Because AED units are relatively expensive, it may be cost prohibitive to equip a large building or area with a sufficient number of AEDs to ensure the close proximity of an AED to a cardiac arrest victim. However, a large building or area may be outfitted with many lower cost rescue kits 36. In the case of a rescue attempt on a victim, a first rescuer can quickly obtain a rescue kit 36 and begin CPR with device 10 while a second rescuer can retrieve an AED 12 from a central location in the building or area. As AED 12 gets into communication range with device 10, device 10 and AED 12 begin communicating via communicator 30. AED 12 can then immediately begin providing prompts to a first rescuer using audio speaker 32 and/or visual display 34. Once first electrode 38 and second electrode 40 of AED 12 are attached to a victim, AED 12 may also prompt a rescuer using audio speaker 32 and/or visual display 34 to momentarily cease chest compressions while a defibrillation shock is administered.

Figure 4:
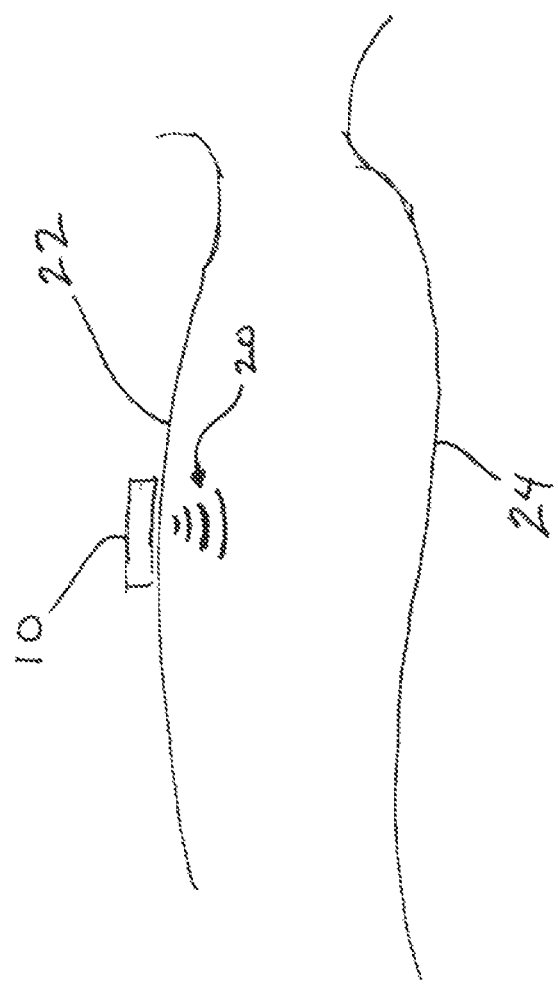
FIG. 4 is a side view of the measurement device applied to a patient.
Figure 6:
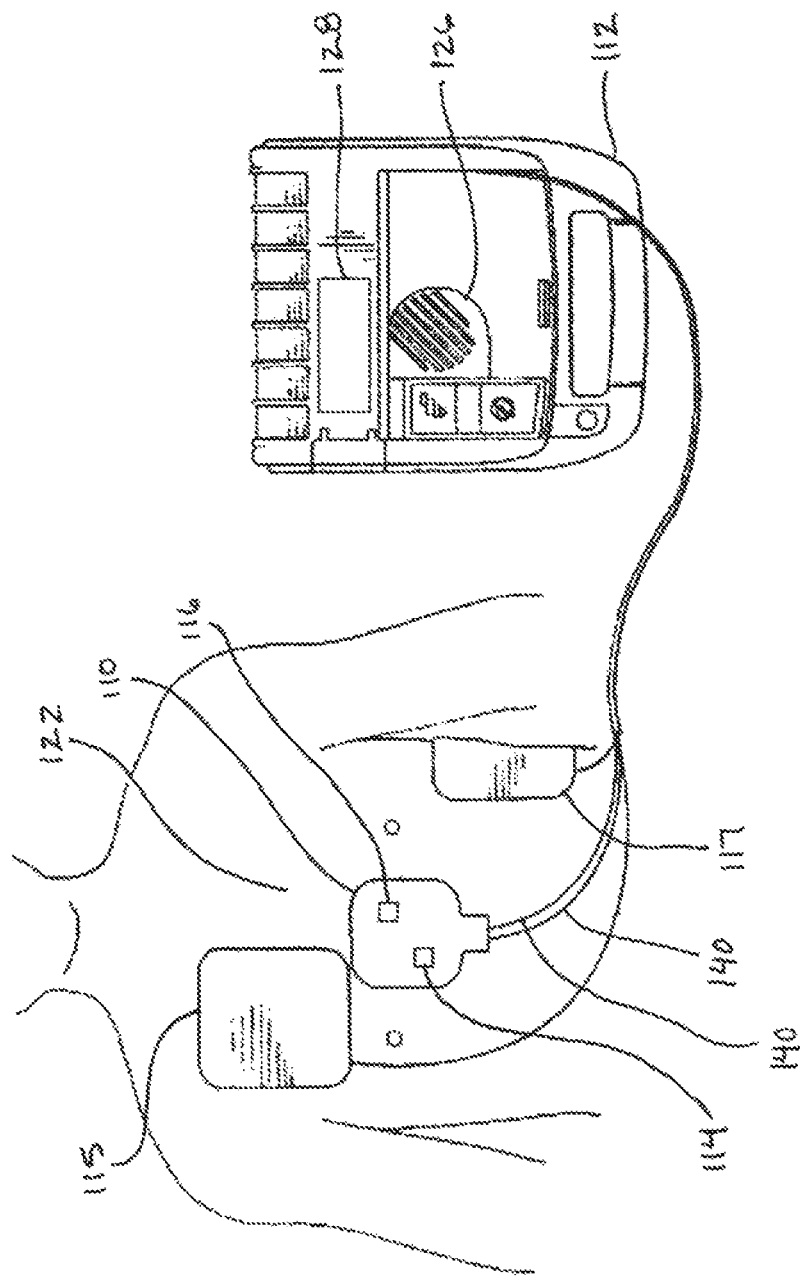
FIG. 6 is a perspective view of a measurement device applied to a patient being used with an automatic external defibrillator according to one embodiment of the present invention.
Figure 8:
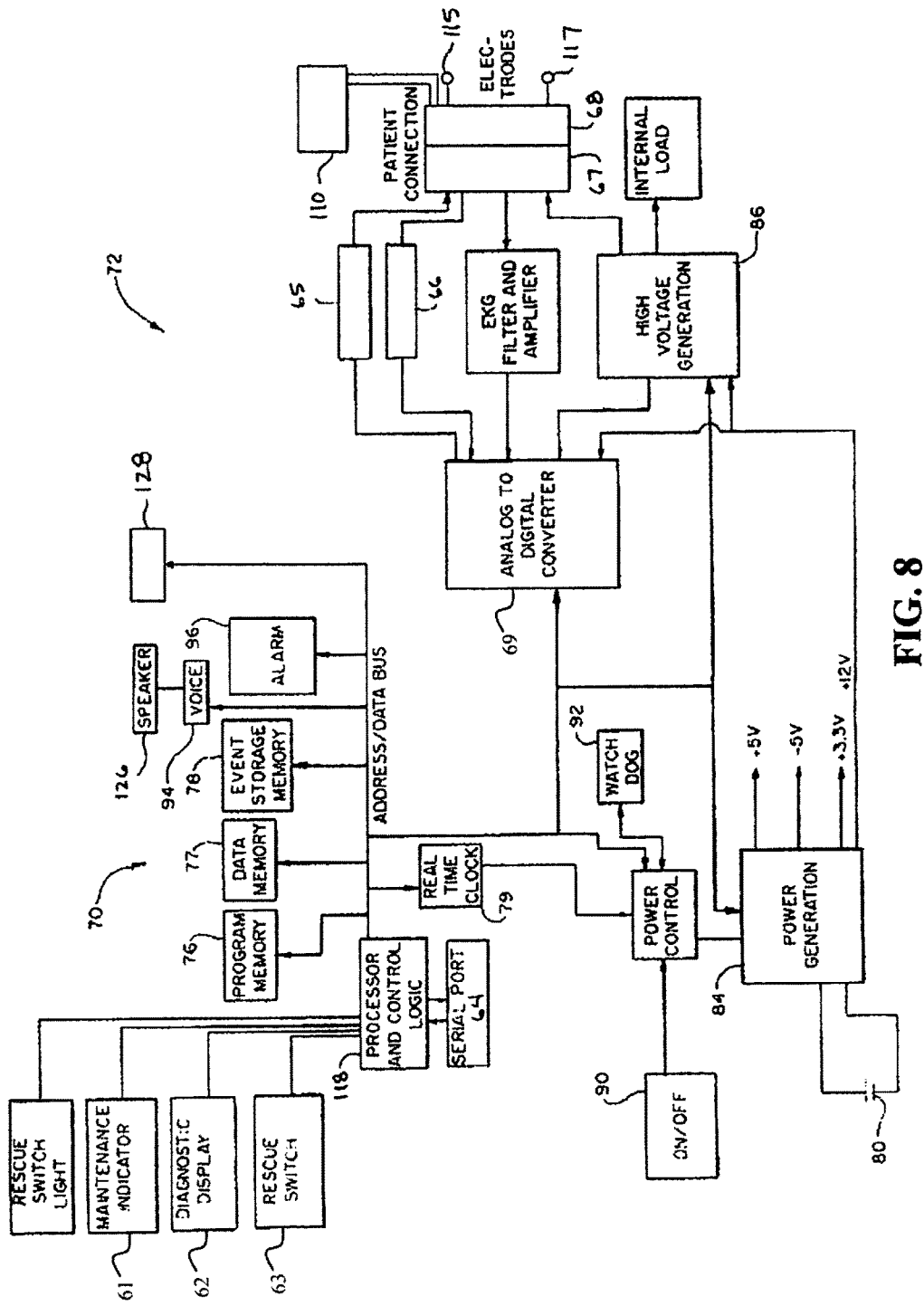
FIG. 8 is a block diagram of an automatic external defibrillator.

In another embodiment of the present invention depicted in FIG. 6, a chest compression detection device 110 is provided as part of an AED 112. Device 110 is removably coupled to AED 112 with wires 140. AED 112 includes a first electrode 115, a second electrode 117, and a processor 118 as depicted in FIG. 8. Device 110 includes a transmitter 114 and a receiver 116, whereby device 110 is adapted to emit ultrasonic pulse 20 from transmitter 114 into a patient's chest 122 and receive pulse 20 at receiver 116 subsequent to pulse 20 being reflected off a patient's spine 24, as shown in FIG. 4. The time elapsed between the transmitting and the receiving of a pulse 20 is used by processor 118 to calculate the distance traveled by pulse 20. By collecting data of the distance traveled by many successive pulses, processor 118 can determine the distance that a chest 122 is being compressed. In one embodiment, the number of pulses 20 emitted per second is sufficient to give processor 18 sufficient data to accurately calculate chest compression depth.

Once processor 118 has calculated chest compression depth, processor 118 compares that depth to a desired range of compression depth (ideally between one and one half (1.5) inches and two (2) inches.) If processor 118 determines that chest 122 is not being compressed enough, processor 118 causes AED 112 to provide feedback to a rescuer performing chest compressions. The prompt may be a voice prompt stating "push harder," or other feedback prompt using an audio speaker 126, or may be a visual prompt using visual display 128, or both. If processor 118 determines that chest 122 is being compressed too much, feedback may be provided to the rescuer with a voice prompt stating "push softer" using speaker 126, or a visual prompt using visual display 128, or both.

Figure 7:
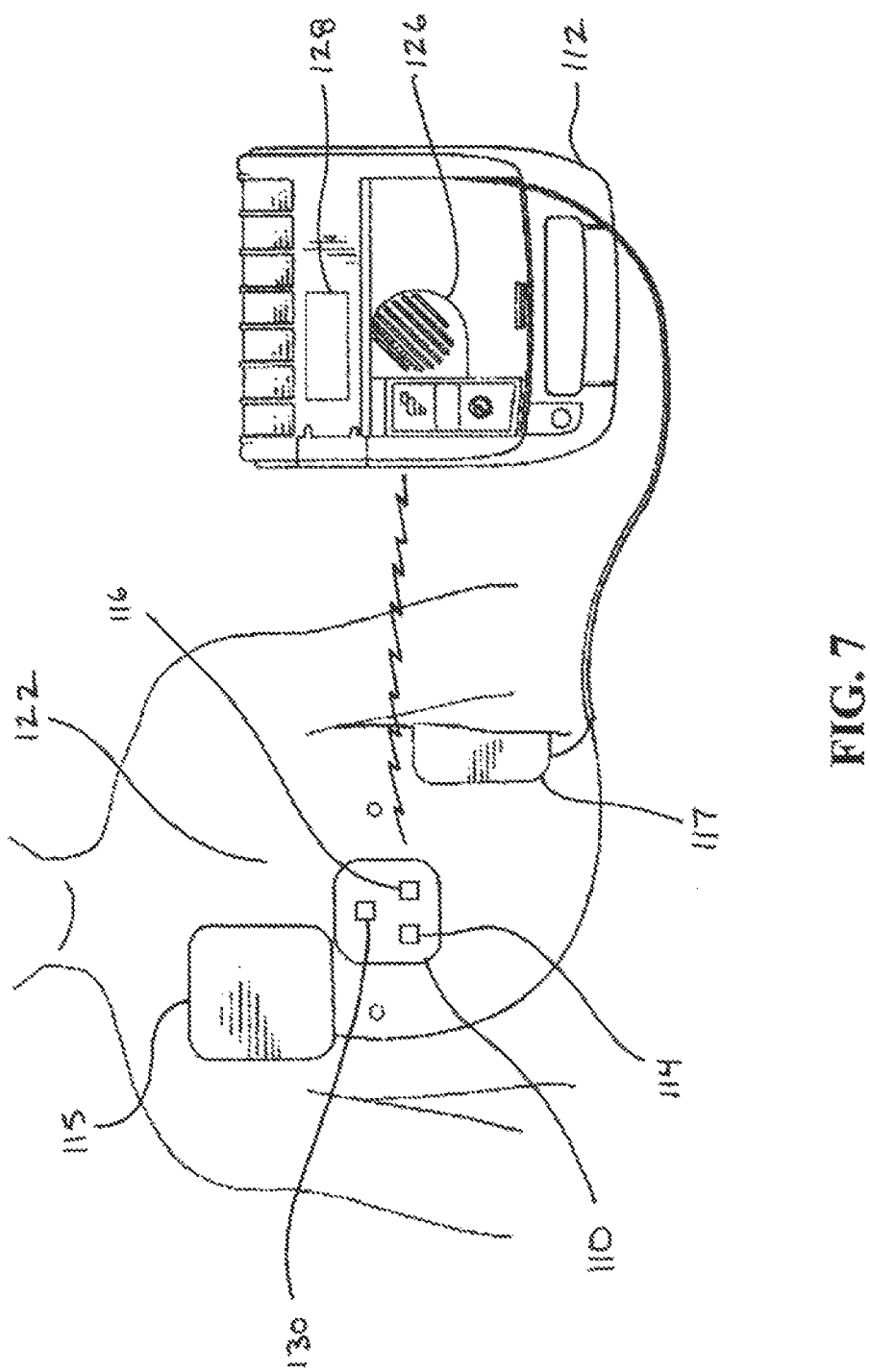
FIG. 7 is a perspective view of a measurement device applied to a patient being used with an automatic external defibrillator according to one embodiment of the present invention.

Processor 118 is also adapted to monitor the rate at which chest compressions are given, and provide feedback to a rescuer if the rate of chest compressions falls outside of a predetermined range of rates. If the rate of chest compressions being delivered by the rescuer is less than the desired range, processor 118 causes AED 112 to provide feedback to the rescuer to increase the rate of compressions. Such feedback may be a voice prompt stating "push faster," or other audible prompt from speaker 126, a visual prompt provided by visual display 128, or other feedback. If the rate of chest compressions being delivered by the rescuer is greater than the desired range, processor 118 causes AED 112 to provide feedback to the rescuer to decrease the rate of compressions. Such feedback may be a voice prompt stating "push slower," or other audible prompt from speaker 126, a visual display provided by visual display 128, or other feedback. In an alternative embodiment depicted in FIG. 7, device 110 lacks wires 140, but includes a wireless means for transmitting data to AED 112, such as, for example, a wireless communicator 130, wherein said wireless means may employ acoustic signals, optical signals, BLUETOOTH® wireless technology standard that uses short-wavelength ultra high frequency waves, IR, or RF.

In one embodiment, AED 112 includes an electrical system such as that disclosed in U.S. Pat. No. 6,125,299 to Groenke et al., which is hereby incorporated by reference. FIG. 8 is a block diagram of electrical system 70 of AED 112. A digital microprocessor-based control system 72 is used for controlling overall operation of AED 112 and for delivering a defibrillation shock pulse through electrodes 115 and 117 via connector 67 and lead wires. The electrical control system 72 further includes an impedance measuring circuit for testing the interconnection and operability of electrodes 115 and 117 to detect several faults. Control system 72 includes a processor 118 interfaced to program memory 76, data memory 77, event memory 78 and real time clock 79. The operating program executed by processor 118 is stored in program memory 76. Electrical power is provided by the battery 80 which is removably positioned within the battery compartment of AED 112 and is connected to power generation circuit 84.

Power generation circuit 84 is also connected to lid switch 90, watch dog timer 92, real time clock 79, and processor 118. Lid switch 90 such as, for example, a Hall-effect or magnetic read relay switch, provides signals to processor 118 indicating whether the lid of AED 112 is open or closed. Data communication port 64 is coupled to processor 118 for two-way serial data transfer using an RS-232 protocol. Rescue switch 63, maintenance indicator 61, the indicator lights of diagnostic display panel 62, the voice circuit 94, and piezoelectric audible alarm 96 are also connected to processor 118. Voice circuit 94 is connected to speaker 126. In response to voice prompt control signals from processor 118, circuit 94, and speaker 126 generate audible voice prompts for consideration by a rescuer.

High voltage generation circuit 86 is also connected to and controlled by processor 118. Circuits such as high voltage generation circuit 86 are generally known, and disclosed, for example, in the commonly assigned Persson et al. U.S. Pat. No. 5,405,361, which is hereby incorporated by reference. In response to charge control signals provided by processor 118, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 118, high voltage generation circuit 86 is operated in a discharge mode during which the capacitors are discharged in series by another set of semiconductor switches (not separately shown) to produce the high voltage defibrillation pulses. The defibrillation pulses are applied to the patient by electrodes 115 and 117 through connector 67 connected to the high voltage generation circuit 86.

Impedance measuring circuit 66 is connected to both connector 67 and real time clock 79. Impedance measuring circuit 66 is interfaced to processor 118 through analog-to-digital (A/D) converter 69. Impedance measuring circuit 66 receives a clock signal having a predetermined magnitude from clock 79, and applies the signal to electrodes 115 and 117 through connector 67. The magnitude of the clock signal received back from electrodes 115 and 117 through connector 67 is monitored by impedance measuring circuit 66. An impedance signal representative of the impedance present across electrodes 115 and 117 is then generated by circuit 66 as a function of the ratio of the magnitudes of the applied and received clock signals (i.e., the attenuation of the applied signal).

For example, if electrodes 115 and 117 within an unopened electrode package are connected by the lead wires and connector 68 is properly connected to connector 67 on AED 112, a relatively low resistance (e.g., less than about 10 ohms) is present across electrodes 115 and 117. If the hydrogel adhesive on electrodes 115 and 117 is too dry, or the electrodes 115 and 117 are not properly positioned on the patient, a relatively high resistance (e.g., greater than about two hundred fifty ohms) will be present across the electrodes 115 and 117. The resistance across electrodes 115 and 117 will then be between about twenty-five and two hundred fifty ohms when fresh electrodes 115 and 117 are properly positioned on the patient with good electrical contacts. It should be noted that these resistance values are given as exemplary ranges and are not meant to be absolute ranges. The impedance signal representative of the impedance measured by circuit 66 is digitized by A/D converter 69 and provided to processor 118.

Impedance measuring circuit 65 is connected to connector 67 and real time clock 79, and is interfaced to processor 118 through analog-to-digital (A/D) converter 69. Impedance measuring circuit 65 receives a clock signal having a predetermined magnitude from clock 79, and applies the signal to chest compression detection device 110 through connector 67. The magnitude of the clock signal received back from device 110 through connector 32 is monitored by impedance measuring circuit 65. An impedance signal representative of the impedance present across device 110 is then generated by impedance measuring circuit 65 as a function of the ratio of the magnitudes of the applied and received clock signals (i.e., the attenuation of the applied signal). The impedance signal representative of the impedance measured by circuit 65 is digitized by A/D converter 69 and provided to processor 118.

Figure 9:
FIG. 9 is a perspective view of a sensor for use with an embodiment of the present invention.

Referring now to FIG. 9, the present invention may also incorporate a pulse oximetry sensor 142. Sensor 142 is operably coupled to AED 112, and is placed on a victim's fingertip, earlobe, or other relatively thin part of a victim's body. Sensor 142 utilizes selected wavelengths of light to noninvasively determine the saturation of oxyhemoglobin ($SpO_2$) in a victim's blood. Based on $SpO_2$ levels, an estimate of the oxygen content of a victim's blood can be determined. Sensor 142 is utilized while chest compressions are administered by a rescuer. Processor 118 receives information from sensor 142, and compares oxygen level readings to a desired range of oxygen levels. Low oxygenation may be due to not compressing the chest of a victim far enough, or at a fast enough rate. In the event that oxygen levels from sensor 142 are too low, processor 118 causes AED 112 to provide feedback to the rescuer to increase the depth of, or rate of compressions. Such feedback may be a voice prompt from speaker 126 stating "push harder" or "push faster," a visual prompt provided by visual display 128, or other feedback. Conversely, high oxygenation may be due to compressing the chest of a victim too far, or at too fast of a rate. In the event that oxygen levels from sensor 142 are too high, processor 118 causes AED 112 to provide feedback to decrease the depth of, or rate of compressions. Such feedback may be a voice prompt from speaker 126 stating "push softer" or "push slower," a visual prompt provided by visual display 128, or other feedback.

Figure 10:
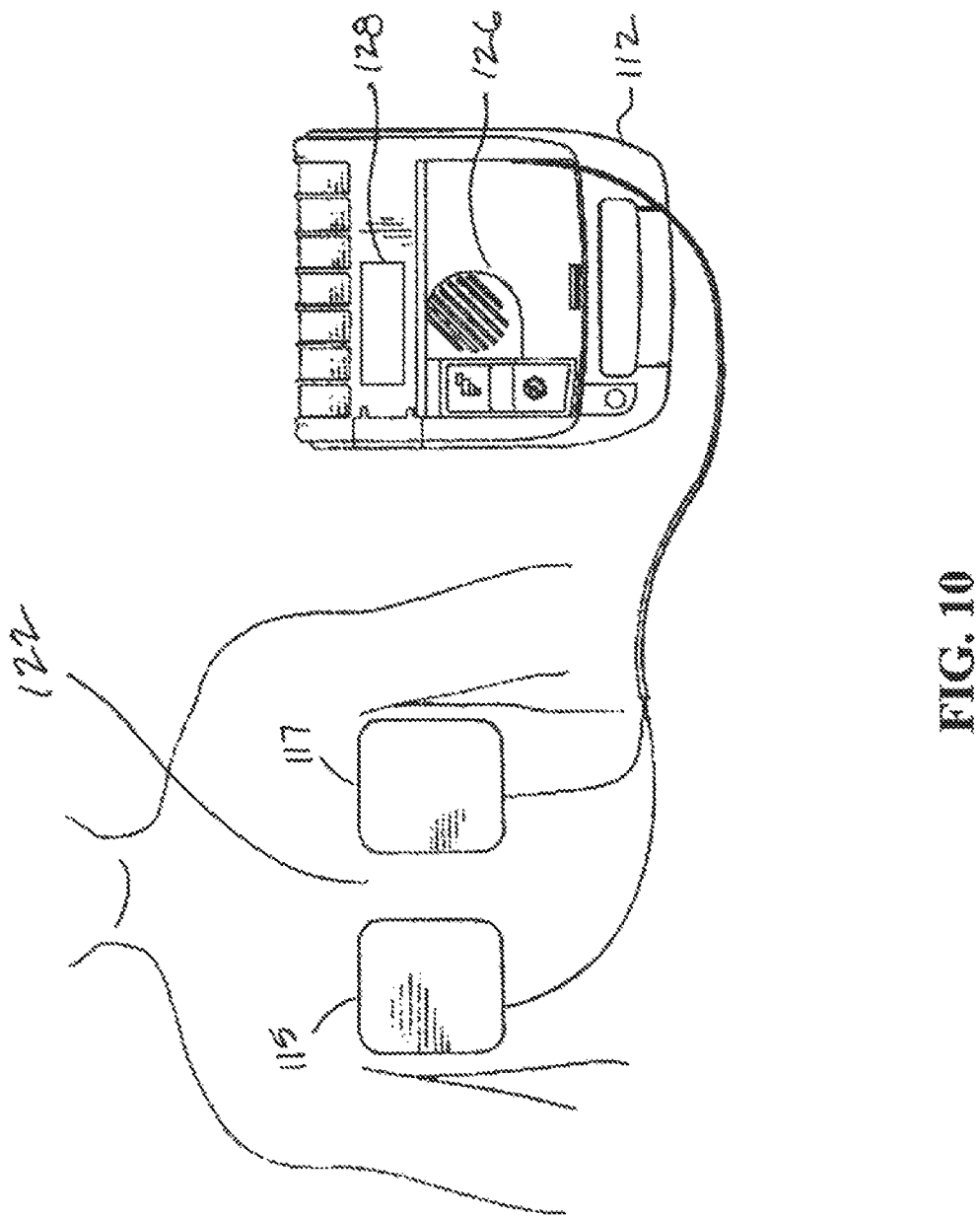
FIG. 10 is a perspective view of an automatic external defibrillator incorporating a measurement device within a pair of electrodes according to one embodiment of the present invention.

Referring now to FIG. 10, a further embodiment of the present invention is shown. Rescuers may be reluctant to conduct chest compressions while putting their hands on an electric device, out of fear of electrocution. Although accidental electrocution is highly improbable, the embodiment depicted in FIG. 10 does not require a rescuer to conduct chest compressions while pushing on an electronic chest compression detection device. Rather, first electrode 115 is adapted to include a signal transmitter 114, and second electrode 117 is adapted to include a signal receiver 116. First electrode 115 and second electrode 117 are operably coupled to processor 118 in AED 112. Pulse 20 (not shown) is emitted from transmitter 114 in first electrode 115, triangulated off of spine 124, and received by receiver 116 in second electrode 117. Electrodes 115 and 117 may be placed on a victim's chest 122 as shown in FIG. 10.

Alternatively, one electrode may be placed on a victim's chest 122 generally over the heart, while the other electrode is placed on a victim's back, such that the two electrodes and the heart are inline, as shown in FIG. 11. In such an arrangement, transmitter 114 in electrode 115 directs a pulse 20 towards receiver 116 in electrode 117, and pulse 20 is not reflected before being received. Further, those skilled in the art will readily recognize that electrodes 115 and 117 and/or chest compression detection device 110 may be placed in locations on a patient other than those explicitly shown in the figures or described herein without deviating from the spirit or scope of this invention.

In order to enhance the reflectivity of pulse 20, a reflector pad may be used in conjunction with all embodiments of the present invention. The reflector pad may be placed generally proximate the victim's back and is adapted to increase the reflectivity of pulse 20, and thereby increase the ability of receiver 116 to receive the reflected pulse 20.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

The invention claimed is:

1. A method of performing cardiopulmonary resuscitation on a patient comprising the steps of:
   providing a compression detection device proximate the sternum of the patient such that the device moves in unison with the chest of the patient during compression of the chest;
   broadcasting an ultrasonic pulse signal from the compression detection device;
   receiving the ultrasonic pulse signal at the compression detection device;
   compressing the chest of a patient with the compression detection device;
   using a processor operably in communication with the compression detection device to determine from the ultrasonic pulse signal a series of measurements of compression distance of the chest relative to the spine of the patient as the step of compressing the chest of the patient is performed; and
   automatically providing feedback to a rescuer performing the step of compressing the chest of the patient as part of cardiopulmonary resuscitation in response to the series of measurements that advises the rescuer whether the step of compressing the chest is being performed within a predetermined set of guidelines.

2. The method of claim 1, wherein the step of broadcasting an ultrasonic pulse signal from the compression detection device further comprises broadcasting an ultrasonic pulse signal from the compression detection device into the chest towards the spine of the patient.

3. The method of claim 2, wherein the step of receiving the ultrasonic pulse signal at the compression device further comprises receiving the ultrasonic pulse signal at the compression device following reflection of at least a portion of the ultrasonic pulse signal off of the spine of the patient.

4. The method of claim 3 further comprising:
   using the processor to determine a timing associated with compression of the chest based on the series of measurements of compression of the chest; and
   automatically providing feedback to the rescuer performing the step of compressing the chest of the patient as part of cardiopulmonary resuscitation in response to the series of timing that advises the rescuer whether the step of compressing the chest is being performed within a predetermined set of guidelines for a recommended timing of chest compressions for cardiopulmonary resuscitation.

5. The method of claim 4, wherein the guidelines are selected from the group consisting of chest displacement, compression rate, and blood oxygen levels.

* * * * *